United States Patent [19]
Nara

[11] Patent Number: 4,969,199
[45] Date of Patent: Nov. 6, 1990

[54] APPARATUS FOR INSPECTING THE MOLDED CASE OF AN IC DEVICE

[75] Inventor: Seietsu Nara, Yokohama, Japan

[73] Assignee: Kabushiki Kaisha Toshiba, Kawasaki, Japan

[21] Appl. No.: 19,783

[22] Filed: Feb. 27, 1987

[30] Foreign Application Priority Data

Feb. 28, 1986 [JP] Japan .................................. 61-41671
Feb. 28, 1986 [JP] Japan .................................. 61-41672
Feb. 28, 1986 [JP] Japan .................................. 61-41673
Feb. 28, 1986 [JP] Japan .................................. 61-41674
Feb. 28, 1986 [JP] Japan .................................. 61-41675

[51] Int. Cl.$^5$ .......................................... G06K 9/00
[52] U.S. Cl. ...................................... 382/8; 358/106; 382/22
[58] Field of Search ............... 382/8, 52, 22; 358/101, 358/106, 107

[56] References Cited

U.S. PATENT DOCUMENTS 4,334,241  6/1982  Kashioka et al. ...................... 382/8
4,525,747  6/1985  Sakai et al. ........................... 382/52
4,644,410  2/1987  Schlichtig ............................. 382/52
4,670,788  6/1987  Ozaki ................................... 358/101
4,696,047  9/1987  Christian et al. ..................... 382/8
4,737,845  4/1988  Susuki et al. ......................... 382/8

Primary Examiner—David K. Moore
Assistant Examiner—Joseph Mancuso
Attorney, Agent, or Firm—Cushman, Darby & Cushman

[57] ABSTRACT

An inspection apparatus includes a device which prepares a circumscribing line of an object to be inspected from pictured image information of the inspected object, and a device which judges the quality of the inspected object from the image information on a portion of the inspected object defined by the circumscribing line prepared by the circumscribing line preparation device. The inspection apparatus may include a device which detects an inclination angle of a nondefective article with respect to a predetermined reference line from pictured image information of the nondefective article, said nondefective article serving as a reference which has the same configuration as the inspected object and registers the inclination angle as a reference angle, and a device for inspecting the quality of the inspected object based on the reference angle in the reference angle detecting and registering device. Moreover, the inspection apparatus may include a device which memorizes pictured image information of the object to be inspected by quantizing it, a device which rotates the quantized image information of the inspected object that is memorized in the quantization and memory device, and a device which memorizes the quantized image information rotated by the image information rotation device after making it multi-valued.

11 Claims, 12 Drawing Sheets

FIG. 11

16 BITS

| | |
|---|---|
| 0 | DETECTION FLAG CODE |
| 1 | ADDRESS OF BLOCK START |
| 2 | LENGTH IN X DIRECTION |
| 3 | LENGTH IN Y DIRECTION |
| 4 | START BIT NO |
| 5 | DETECTION FLAG CODE |
| 6 | ADDRESS OF BLOCK START |
| 7 | |
| ⋮ | |

FIG. 12

DATA TABLE FOR HORIZONTAL PROJECTION

| |
|---|
| DETECTION FLAG CODE |
| ADDRESS OF BLOCK START |
| LENGTH IN X DIRECTION |
| LENGTH IN Y DIRECTION |
| HORIZONTAL PROJECTION DATA |
| HORIZONTAL PROJECTION DATA |
| HORIZONTAL PROJECTION DATA |
| HORIZONTAL PROJECTION DATA |
| HORIZONTAL PROJECTION DATA |
| HORIZONTAL PROJECTION DATA |
| HORIZONTAL PROJECTION DATA |
| HORIZONTAL PROJECTION DATA |
| HORIZONTAL PROJECTION DATA |

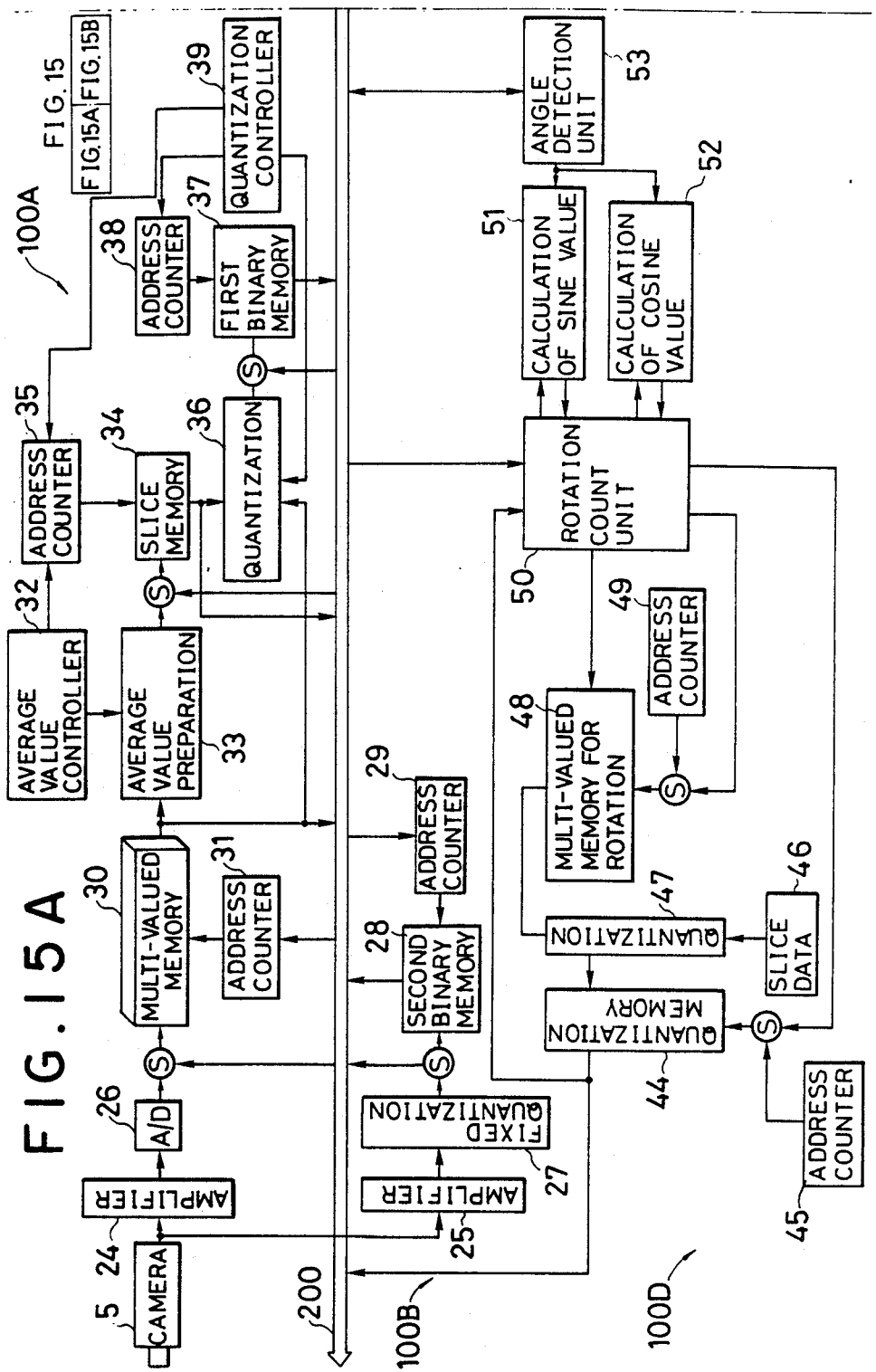

FIG.23
T TA7664P ·4P
FIG.24
T TA7664P ·4P
FIG.25
T TA7664P ·4P
FIG.26
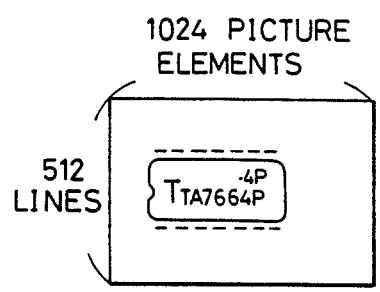
1024 PICTURE ELEMENTS
512 LINES
FIG.27
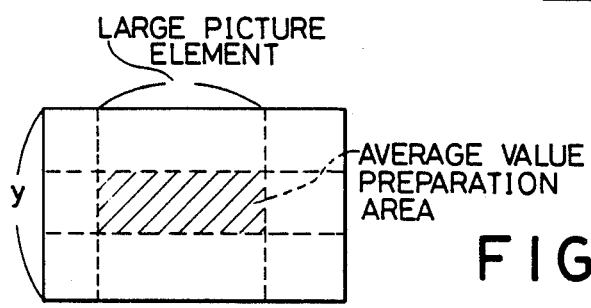
LARGE PICTURE ELEMENT
AVERAGE VALUE PREPARATION AREA
AVERAGE VALUE S PER LINE
$S_{yn} = \dfrac{\Sigma A/D}{X}$
FIG.28
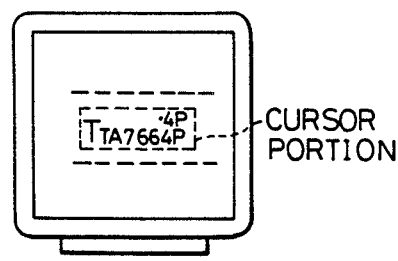
CURSOR PORTION FIG. 29
T TA7664P  ·4P
FIG. 30
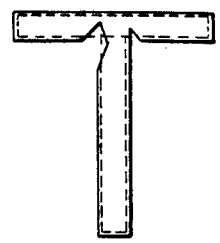
FIG. 31
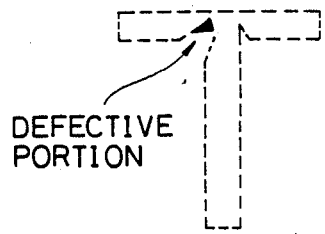
DEFECTIVE PORTION
FIG. 32
| KIND | NO |
|---|---|
| START ADDRESS | |
| X SIZE (WORD NUMBER) | |
| Y SIZE | |
| STANDARD PATTERN | |
| SOMEWHAT THICK PATTERN | |
| SOMEWHAT THIN PATTERN | |
| KIND | NO |
FIG. 33
| KIND | NO |
|---|---|
| ANGLE | θa |
| ANGLE | θb |
| ANGLE | θ1 |
| KIND | NO |
| ANGLE | θa' |
| ANGLE | θb' |
| ANGLE | θ1' |

APPARATUS FOR INSPECTING THE MOLDED CASE OF AN IC DEVICE

BACKGROUND OF THE INVENTION

1. Field of the Invention

The present invention relates generally to the visual inspection of objects, and, more particularly, to an inspection apparatus for inspecting the visual appearance of an object, such as an integrated circuit (IC) package, based upon information derived from images taken of the inspected object.

2. Description of the Prior Art

For integrated circuit parts, such as IC packages, inspection of their electrical performance characteristics and their visual appearance characteristics is very important. Visual features that are inspected include, for example, marks, symbols, printed alphanumeric characters, and/or other indicia provided on the integrated circuit package case to display, for example, the name of the product, the lot number, the name of the manufacturer, and so on, with the inspection seeking to determine if these marks, symbols, characters, and/or indicia are formed in a preferred alignment, such as along a straight line, without being crooked or otherwise misaligned; to determine if there are voids, rubbing-offs, chips, scratches, and so on in these marks; and to determine if there are scratches, chips, cracks, and blowouts on the molded integrated circuit case, and so forth.

The visual appearance inspections are very minute and delicate, requiring highly developed judgement skills on the part of the inspector, and, accordingly, it has been very difficult to implement a mechanical device for performing the inspection traditionally performed by skilled workers. When inspections are carried out by skilled workers, the inspection tends to lack reliability due to the differences in the visual criteria applied by different workers. In addition, the inspection speed is relatively low for human inspectors and the inspection operation cannot be performed continuously over a long period of time. Moreover, even for the same worker, the visual inspection criteria will vary depending upon the length of the inspecting period and the mood or disposition of the inspector.

In addition to the visual method of inspection performed by a skilled worker, it is known to perform an inspection of an object, such as an integrated circuit package, using an apparatus which uses information derived from an image formed from the object to be inspected. However, problems and other drawbacks have been associated with prior art apparatus for carrying out an inspection mechanically, these problems including insufficient recognition accuracy in assessing the quality of the appearance from the image information, insufficient inspection rates, and/or a lack of reliability. More specifically, for a visual appearance inspection it is preferred from the standpoint of efficiency during the manufacturing process to perform the inspection while the items to be inspected are being transported by a transporting device, such as a conveyor. However, when an item is transported by a conveyor, the reliability of inspection result is not sufficiently high because the inspection apparatus is not able to cope completely with various undesired situations, such as the occurrence of unevenness in the transportation of the inspected objects or an unintended change in the orientation of the object from a predetermined position or alignment due to a shift in position caused by vibrations or the like. While the transport speed of the objects to be inspected can be reduced to avoid the above-mentioned drawbacks, the resulting decrease in the overall inspection capability of the apparatus is inconsistent with the desired goal of reliable time and cost efficient inspection. In addition, the prior art apparatus is unable to accommodate a plurality of different types of objects to be inspected, and, accordingly, is not economically efficient where different types of objects are to be inspected.

SUMMARY OF THE INVENTION

It is a principal object of the present invention, among others, to provide an inspection apparatus that is capable of performing a fast and accurate inspection of an object to be inspected and, in particular, the casing portion of the object to be inspected.

It is another object of the present invention to provide an inspection apparatus which is capable of performing a fast and accurate inspection of an object to be inspected and, in particular, a mark or other indicia provided on the object to be inspected.

It is a further object of the present invention is to provide an inspection apparatus which is capable of performing visual appearance inspection of an object to be inspected in an efficient, fast, and accurate manner.

In view of these objects, and others, the present invention provides an inspection apparatus which performs an inspection of an object based on information from an image formed from the object to be inspected, the inspection apparatus comprising circumscribed line preparation means which draws a circumscribed line for the casing portion of the object to be inspected from the image information of the object, and evaluation means for judging the quality of the object to be inspected from the image information regarding the casing portion of the object to be inspected, excluding the circumscribed line made by the circumscribed line drawing means. More particularly, an inspection apparatus which performs an inspection of an object based on information from an image formed from the object to be inspected comprises reference angle detection and registering means for detecting an inclination angle of the object to be inspected with respect to a predetermined reference line, derived from information regarding an image of a nondefective article that has the same components as the object to be inspected and which serves as a reference, and registers the inclination angle as a reference angle, and inspection means which inspects the object to be inspected based on the reference angle in the reference angle detection and registering means.

Furthermore, in an inspection apparatus which performs an inspection of an object to be inspected based on the information regarding an image formed from the object to be inspected, the present inspection apparatus comprises quantized memory means which memorizes by quantizing information of an image taken from the object to be inspected, image information rotating means which rotates the quantized image information of the object to be inspected that is memorized in the quantized memory means, and multi-valued memory means which memorizes the quantized information which is rotated by the image information rotating means by rendering the information multi-valued.

In the disclosed embodiment of the present invention, dual-in-line (DIP) integrated circuit packages are inspected. The integrated circuits include a molded case with connecting pins or leads extending from opposite sides of the molded case. In addition, a 'mark area' is provided on the molded case and typically includes various symbols, alphanumeric characters, and other indicia that are printed or otherwise placed within the mark area in a preferred alignment relative to the molded case. Each integrated circuit is visually inspected for the presence of scratches, pits, voids, etc., in the molded case; connecting pins that are bent inward, bent outward, or otherwise misaligned; the alignment of the mark area; and the quality of the indicia within the mark area.

In order to inspect integrated circuits, a defect-free integrated circuit is imaged using one or more video cameras with the image signal processed to provide reference information for storage in a 'dictionary' memory, which information serves as a reference for comparison with information observed from a to-be-inspected integrated circuit. The reference information includes the angular orientation of the mark area, designated by the reference angle $\Theta a$, and the angular orientation of the connecting pins, designated by reference angle $\Theta b$, relative to a base line.

A image signal of to-be-inspected integrated circuit provided by the observing camera, which image is defined by a plurality of image lines of a fixed number of pixels each, is concurrently processed for storage in a first binary image memory and a second binary image memory. The image processed for storage in the second binary image memory is processed to emphasize the position of the connecting pins extending from the sides of the molded case. The image stored in the second binary image memory, which emphasizes the image of the connecting pins, is loaded into an image processing memory and is examined to determine the position of the connecting pins so as to define a circumscribing boundary line that contains the molded case and excludes the connecting pins. All image information exteriorly of the molded case boundary line is remove, i.e., cleared, from the image memory leaving only image information relating to the molded case and any defects associated with the molded case, including scratches, voids, pits, and the like. In order to detect the presence of any defects in the molded case, the image data is orthogonally projected on respective vertical and horizontal axes in such a manner that projected defects appear as relatively darker portions of the projected image. When detected, the defects are quantified in terms of their height and width and the height and width sum is evaluated to determine if the detected defects are within acceptable limits.

The orientation of the connecting pins are evaluated to determine if one or more pins are bend inward or outward, or otherwise misaligned, using the image information stored in the second binary image memory. The apparent height and width of each connecting pin are determined from the stored image information and compared with acceptable reference height and width information, previously obtained from a defect-free integrated circuit, to determine if an observed pin is within acceptable specification.

The marks or other indicia within the mark area of the molded case are inspected by processing the video image to determined the observed angular orientation of the mark area, designated by the reference angle $\Theta d$, and effecting a comparison with the reference angular orientation of the mark area, angle $\Theta a$, previously obtained from a defect free integrated circuit. If the observed and reference angles, $\Theta a$ and $\Theta d$, do not coincide, which indicates that the observed integrated circuit is skewed or otherwise misaligned, the image of the observed integrated circuit is rotated to effect coincidence. The angular relationship of the mark area to the connecting pins is evaluated to determine if the mark area is unacceptably skewed relative the pins, and the image of the mark area of the observed integrated circuit is evaluated by pattern matching with the previously stored image of a defect-free integrated circuit with the pattern matching including matching against stored 'dictionary' images that are somewhat larger and smaller than the standard image.

BRIEF DESCRIPTION OF THE DRAWINGS

These and other objects, features, and advantages of the present invention will be more apparent from the following description of the preferred embodiments taken in conjunction with the accompanying drawings in which:

FIG. 11 is a table which shows the result of the block detection by perpendicular projection of the integrated circuit image information formed with the apparatus of FIG. 1;

FIG. 12 is a table prepared by horizontal projection of integrated circuit image information formed by the apparatus of FIG. 1;

FIGS. 15, 15A, and 15B are diagrams of a first recognition portion of another embodiment of the inspection apparatus of the present invention;

FIG. 23 to FIG. 25 are diagrams which show various dictionary reference patterns of a nondefective, that is, defect free, integrated circuit mark pictured with the apparatus of FIG. 1;

FIG. 26 is a multi-valued image diagram of an integrated circuit taken with the apparatus of FIG. 1 and illustrated that the image is constituted by 512 horizontal scan lines, each defined by 1024 pixels;

FIG. 27 is a diagram which shows the method for preparing average values from image information taken with the apparatus of FIG. 1;

FIG. 28 is a diagram which shows the segmenting method of a mark area for the dictionary from image information of a non defective integrated circuit taken with the apparatus of FIG. 1;

FIG. 29 to FIG. 31 are diagrams which show a defective pattern of an integrated circuit mark image taken with the apparatus of FIG. 1;

FIG. 32 and FIG. 33 are diagrams which show the dictionary format of image information of an integrated circuit taken with the apparatus of FIG. 1.

DETAILED DESCRIPTION OF THE PREFERRED EMBODIMENTS

Figure 1:
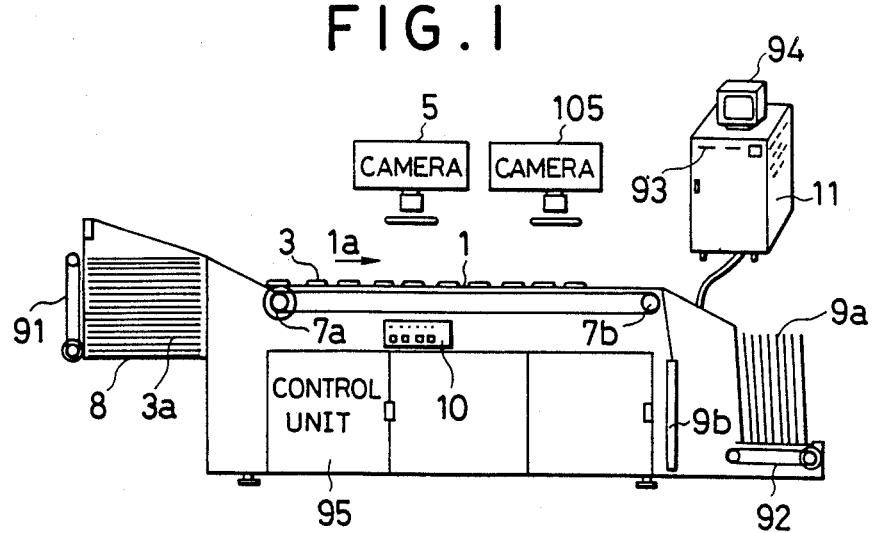
FIG. 1 is a configuration diagram illustrating an overall configuration of an integrated circuit (IC) inspection apparatus in accordance with an embodiment of the present invention.

A first embodiment of an inspection apparatus in accordance with the present invention is presented in FIGS. 1 to 14 with the overall configuration thereof illustrated in FIG. 1. As shown, integrated circuits 3 are transported on a transporting line 1, which includes a centrally located belt conveyor (unnumbered), or the like, with cameras 5 and 105 positioned above the transport line 1 to observe the integrated circuits 3 as they are transported from the left to the right in FIG. 1. The cameras 5 and 105 provide video image signals from which the appearance inspections of the integrated circuits 3 are effected.

The appearance inspection of an integrated circuit 3 is accurately carried out by the integrated circuit inspection apparatus by executing the following functions:

(1) Measurement of a reference angle $\Theta a$ of a printed mark of a defect free integrated circuit and the registration of the reference angle $\Theta a$ in a dictionary (this measurement carried out while transporting a nondefective integrated circuit on the transporting line).

(2) Measurement of a reference orientation angle $\Theta b$ of the connecting pins of a defect free integrated circuit and the registration of the reference angle $\Theta b$ in a dictionary (this measurement carried out while transporting a nondefective integrated circuit on the transporting line).

(3) Measurement of the orientation angle $\Theta c$ of the connecting pins of an integrated circuit to be inspected.

(4) Measurement of the angle $\Theta d$ of the printed marks of an integrated circuit to be inspected.

(5) Inspection of the skew of the printed marks on an integrated circuit to be inspected, based on the reference angles $\Theta a$ and $\Theta b$ obtained from a defect free integrated circuit and the measured angles $\Theta c$ and $\Theta d$ from the inspected integrated circuit.

(6) Inspection for defects, such as rubbing-off and chips, in the printed marks on an integrated circuit to be inspected.

(7) Inspection for defects, such as flaws, whips, and cracks, in the molded case of an integrated circuit to be inspected.

Of the two cameras 5 and 105, camera 5 provided image signal information for performing functions (1) through (6), above, and camera 105 provides image signal information for performing function (7).

As shown in FIG. 1, a pair of rollers 7a and 7b are positioned at opposite ends of the transporting line 1 and carry a transporting belt (unnumbered). A transporting unit is formed by the transporting line 1, the rollers 7a and 7b, the transporting belt, and a motor (not shown). An integrated circuit loader unit 8 is located adjacent the roller 7a and houses stacks of integrated circuit sticks 3a, which contain a large number of integrated circuits 3. The loader unit 8 places integrated circuits 3, on a one by one basis, onto the transporting line 1 to be transported from the left to the right in the direction of the arrow 1a beneath the cameras 5 and 105. A control mechanism 91 located adjacent the loader unit 8 and moves the integrated circuit sticks 3a from the loader unit 8 on a one by one basis to assist in placing integrated circuit sticks 3a onto the transporting line 1.

Integrated circuit housing units 9a and 9b for receiving, respectively, defect-free and defective integrated circuits 3, are located adjacent the roller 7b on the right side of the transporting line 1 in FIG. 1. As explained more fully below, the integrated circuit housing units, 9a, constitutes an unloader unit for housing nondefective integrated circuits, while the other integrated circuit housing unit, 9b, constitutes an unloader unit for housing defective integrated circuits. A control mechanism 92 is provided beneath the unloader unit 9a for controlling the movement of the integrated circuits to the nondefective unit unloader unit 9a.

The components of FIG. 1 are organized to allow the cameras 5 and 105 to observe the integrated circuits 3 and provide a video image, or picture, of the integrated circuits 3 after they are removed from the integrated circuit loader unit 8 and transported on the transporting line 1 in the direction of the arrow 1a. As explained in more detail below, the integrated circuits 3 are sorted into nondefective and defective units by the inspection, which is carried out based on the images taken, and directed to and housed in one of the integrated circuit housing units, 9a or 9b, respectively.

The cameras 5 and 105 are connected by cables or other means (not shown) and supply image information to a recognition unit 11 for recognizing and inspecting the appearance of the integrated circuits 3. The recognition unit 11 inspects the quality of the appearance of the integrated circuits 3 from the image signals, and sorts integrated circuits 3 that are transported on the transporting line 1 to direct them to the nondefective unit unloader unit 9a and the defective unit housing unloader unit 9b, based on the results of the inspection. As will be described in detail below, the recognition unit 11 carries out recognition and inspection of the integrated circuit appearance by the use of various kinds of logic circuits, a CPU, memories, and other circuits. As shown in FIG. 1, the recognition unit 11 is box-shaped and includes floppy disc drives 93 for memorizing various data and other information. A video display 94 is mounted on top of the recognition unit 11 and displays a visual representation of the appearance of the observed integrated circuits.

At about the center of the integrated circuit appearance inspection apparatus, a control panel 10 is provided which is equipped with various keys, lamps, and so forth. The control panel 10 is provided to allow operator control of the integrated circuit appearance inspection apparatus by providing command signals to a control unit 95 to carry out the various functions (1) through (7), described above, or to perform various kinds of other operations.

Figure 2:
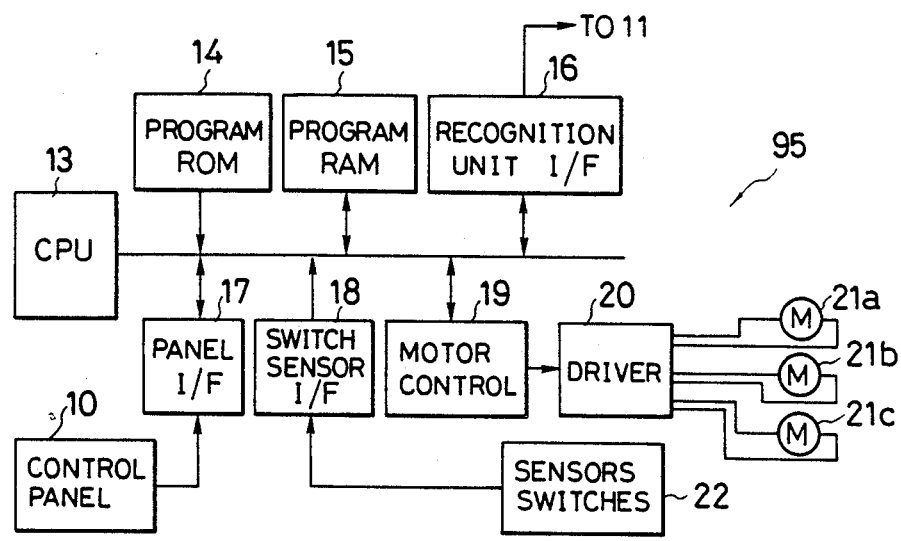
FIG. 2 is a schematic block diagram illustrating the configuration of a control portion of the integrated circuit inspection apparatus of FIG. 1.

FIG. 2 presents a block diagram of the configuration of the control unit 95 of FIG. 1. As shown, the control unit 95 includes a central processing unit (CPU) 13 to which are connected via a bus (unnumbered) a program ROM 14, a program RAM 15, a recognition unit interface 16, a panel interface 17, a switch-sensor interface 18, and a motor controller 19. The recognition unit interface 16 is an interface for connecting the CPU 13 to the recognition unit 11 (FIG. 1) with the recognition unit 11 operated under the control of the CPU 13 via this interface. The panel interface 17 is connected to the control panel 10, and the switch-sensor interface 18 is connected to a switch-sensor unit 22 which consists of various kinds of sensors and switches. In addition, the motor controller 19 is connected via a driver 20 to motors 21a, 21b, and 21c. These motors 21a, 21b, and 21c are used for driving, respectively, the control mechanism 91 for the loader unit 8 at the left in FIG. 1, the roller 7a of the transporting unit, and the control mechanism 92 for the nondefective article unloader unit 9a at the right in FIG. 1. The motors 21a, 21b, and 21 are actuated under the control of the CPU 13 which is actuated by commands provided from the control panel 10 to carry out the operations of removing integrated circuit sticks 3a from the loader unit 8, transporting the integrated circuits on the transporting line 1, and directing them to and housing them in one or the other of the integrated circuit housing units 9a and 9b.

Figure 3:
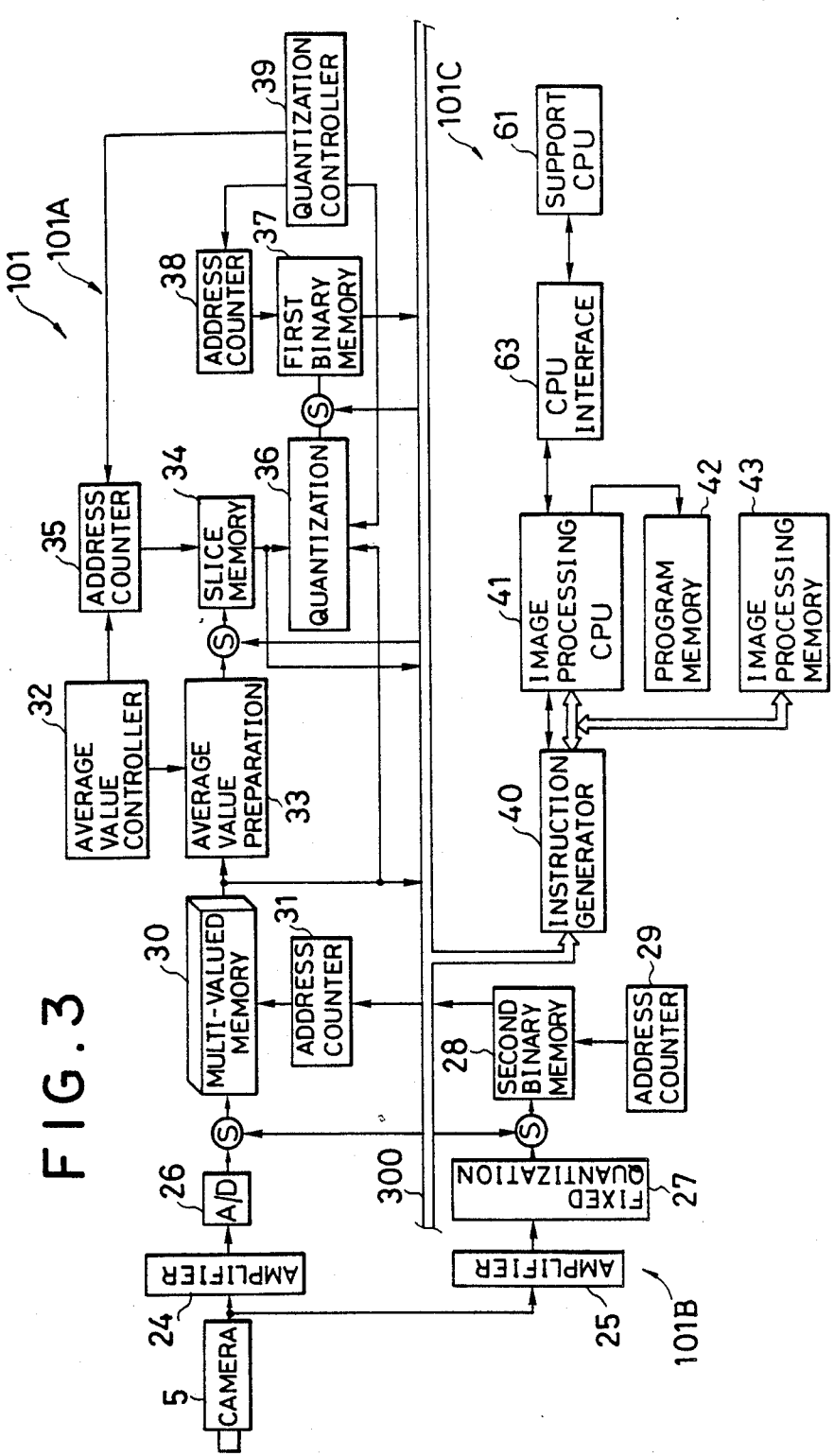
FIG. 3 is a block diagram of a recognition portion of the integrated circuit inspection apparatus of FIG. 1.
Figure 4:
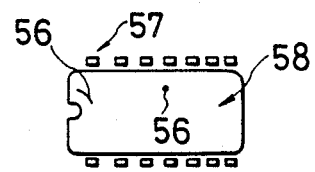
FIG. 4 is a diagram which shows an image of an integrated circuit package having a defect in the molded case portion of the integrated circuit, formed by using the apparatus of FIG. 1.

As shown in the block diagram of FIG. 3, the recognition unit 11 includes the camera 5 located above the transporting line 1 and which observes the appearance of integrated circuits 3 as they pass beneath the camera 5. An image signal of an integrated circuit 3 observed by the camera 5 is amplified by amplifiers 24 and 25, and the amplified signal is supplied to an A/D converter 26 and a fixed quantization unit 27, respectively. The A/D converter 26 effects an analog-to-digital conversion of the image signal of the integrated circuit 3 and provides 8-bit data, representative of 256 possible gradations, and stores the multi-valued data in a multi-valued memory 30 via a selector S. The multi-valued memory 30 is connected to an address counter 31 with the address of the memory 30 designated by the address of the address counter 31. The multi-valued data pattern of an image signal of an integrated circuit 3 that is stored in the multi-valued memory 30 is displayed, for example, as shown in FIG. 4. The multi-valued data from the multi-valued memory 30 thus displayed is supplied to an average value preparation unit 33 where an average value of the multi-valued data only within the molded case of the integrated circuit is calculated.

More specifically, the multi-valued data displayed, as in FIG. 4, for example, for each line of the image are summed, and an average value per picture element (pixel) for the line is calculated by dividing the so-obtained sum by the number of picture elements that constitute the line. Namely, the multi-valued A/D data that are A/D converted for each line are summed and the summed value is divided by the number x of picture elements in each line to obtain an average value $S_{yn} = \Sigma(A/D)/x$. The average value obtained in the average value preparation unit 33 is stored in a slice memory 34 via a selector S. Here, the address of the slice memory 34 is the same as the number of the vertical line of the image. That is, the average value for each line that corresponds to each vertical line is stored in the slice memory 34. The average value stored in the slice memory 34 is supplied to the A/D pattern quantization unit 36 to quantize the multi-valued data that is supplied from the multi-valued memory 30 to the A/D pattern quantization unit 36 with the average values as the slice data. Then, binary image data is formed, and the binary image data is stored from the A/D pattern quantization unit 36 in a first binary memory 37. For these operations, the average value preparation unit 33 is controlled by an average value controller 32, and the slice memory 34 and the first binary memory 37 are supplied with address information from address counters 35 and 38, respectively. In addition, the A/D pattern quantization unit 36 and the address counters 35 and 38 are controlled by a quantization controller 39. The circuit blocks from the amplifier 24, on the left in FIG. 3, to the quantization controller 39, on the right in FIG. 3, described above, constitutes a multi-valued quantization circuit unit 101A which prepares multiple data for an image of the integrated circuit 3 and prepares binary image data from the multiple data.

Figure 5:
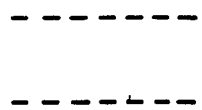
FIG. 5 is an image pattern diagram by fixed quantization which emphasizes the integrated circuit pins, formed with the apparatus of FIG. 1.
Figure 6:
FIG. 6 is a multi-valued image pattern diagram with a defect in the integrated circuit, formed with the apparatus of FIG. 1.
Figure 7:
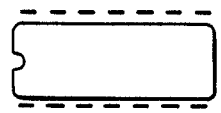
FIG. 7 is a diagram which shows a circumscribed line of the mold casing portion of an integrated circuit, formed with the apparatus of FIG. 1.
Figure 8:
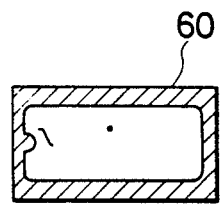
FIG. 8 is a diagram which shows the clear area of the image information of an integrated circuit, formed with the apparatus of FIG. 1.

Concurrently, the image signal of the integrated circuit 3 from the camera 5 is supplied via the amplifier 25 to a fixed quantization unit 27 where it is converted to a binary image signal by a predetermined fixed slice level, and is stored via a selector S in a second binary memory 28 as a binary image signal with address information for the second binary memory provided from an address counter 29. The quantization by a fixed slice level in the fixed quantization unit 27 is carried out so as to emphasize the connecting pins, namely, the image of the leads, and the lead emphasizing image pattern that is obtained in this manner is displayed, for example, as shown in FIG. 5.

The circuit blocks from the amplifier 25, on the left in FIG. 3, to the address counter 29 constitutes a fixed quantization circuit unit 101B which prepares binary image data by giving a fixed quantization to an image signal of the integrated circuit 3 for the purpose of emphasizing the integrated circuit pins in the resulting image signal stored in the second binary memory 28.

The multi-valued quantization circuit unit 101A and the fixed quantization circuit unit 101B are connected respectively to an image bus 300 via various memory units, namely, the multi-valued memory 30, the first binary memory 37 and the second binary memory 28, the selectors S, and other circuits. An image processing CPU 41 is connected to the image bus 300 via an instruction generating unit 40, and is also connected to a program memory 42, an image processing main memory 43, and a support CPU 61 via a CPU interface 63. The image processing CPU 41 controls, along with the program memory 42 and the image processing main memory 43, the overall operation of the recognition unit 11. In addition, the image processing CPU 41 is connected to the display 94 (FIG. 1) where the image of the integrated circuit 3 observed by the camera 5 is displayed under the control of the image processing CPU 41. The circuit blocks from the instruction generating unit 40 to the support and interface CPU's 61 and 63 constitutes a central control unit 101C.

As described above, the recognition unit 11 is constituted by the multi-valued quantization circuit unit 101A, the fixed quantization circuit unit 101B, and the central control unit 101C that are connected mutually via the image bus 300.

Figure 13:
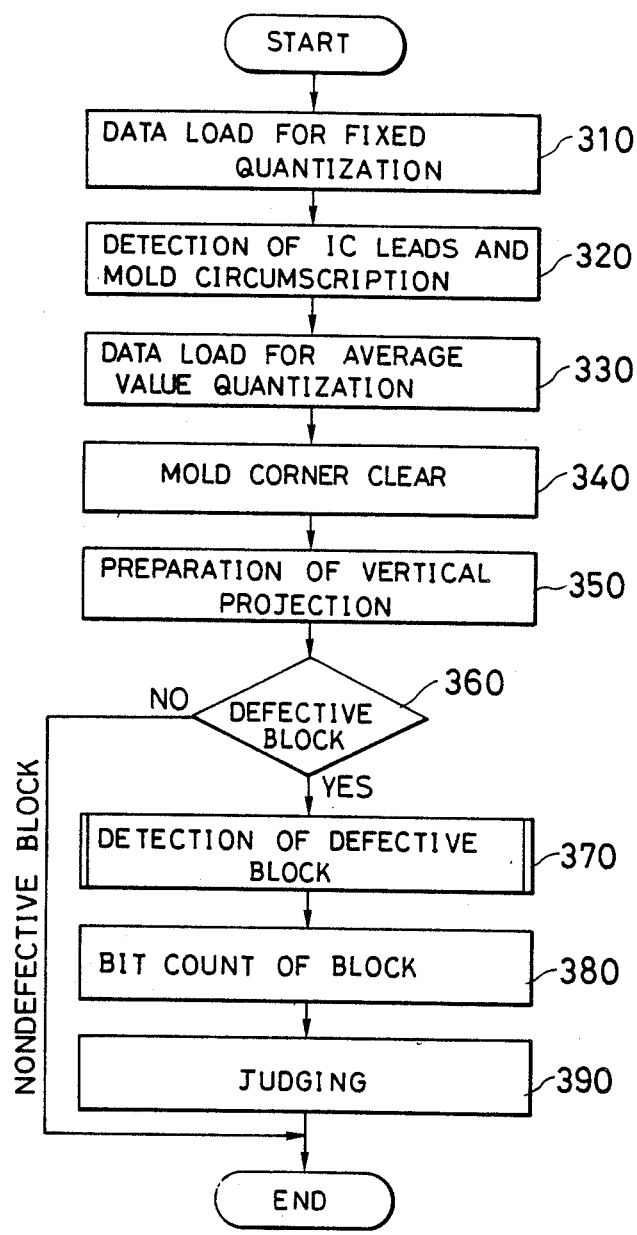
FIG. 13 is a flow chart which shows the operation of the recognition portion of the present invention illustrated in FIG. 3.

The recognition unit 11 shown in FIGS. 1 and 3 operates in accordance with the instruction sequence of FIG. 13 to inspect integrated circuits 3 for scratches, chips, cracks, and other defects in the molded case portion of an observed integrated. Suppose, for example that an integrated circuit 3 to be inspected having scratches 56 in the molded case portion of integrated circuit, as shown in FIG. 4, is transported on the transporting line 1. The image of the observed integrated circuit 3 is supplied by the camera 5, respectively, to the multi-valued quantization circuit unit 101A and the fixed quantization circuit unit 101B. In the multi-valued quantization circuit unit 101A, the image signal from the camera 5 is amplified by the amplifier 24, and is then stored in the multi-valued memory 30 by converting it to a multi-valued image data of one of 256 possible gradations through the A/D converter 26. In addition, the multi-valued image data is converted to binary image data via the average value preparation unit 33 and the A/D pattern quantization unit 36 and is stored in the first binary memory 37.

Concurrently, the image signal from the camera 5 is amplified by the amplifier 25 in the fixed quantization circuit unit 101B, and is then stored in the second binary memory 28 as a binary image data by giving a fixed quantization in accordance with a fixed slice level of the fixed quantization unit 27. The image pattern of a binary image data, which is memorized in the second binary memory after being quantized in the fixed quantization circuit unit 101B according to a fixed slice level, is displayed, for example, in FIG. 5, with emphasis on the connecting pins. In addition, an image pattern of the binary image data, which is memorized in the first binary memory 37 after being quantized in the multi-valued quantization circuit unit 101A according to the average value, is displayed distinctly, for example, the molded case portion of an integrated circuit 3 to identify scratches 56 and the like.

As described above, when a binary image data that is hard processed is memorized in the first binary memory 37 and the second binary memory 28, the binary image data that is quantized by the fixed slice and memorized in the second binary memory 28, namely, the image data with emphasis placed on the connecting pins, is transferred to the image processing main memory 43 (step 310 of FIG. 13).

Figure 9:
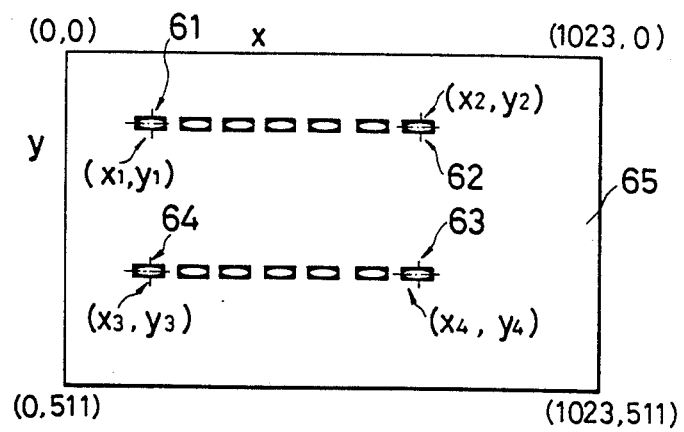
FIG. 9 is a diagram which shows the detection of the integrated circuit lead portion, formed with the apparatus of FIG. 1.

Next, the coordinates of the connecting pins, that is, of the leads, are determined from the image data, and the circumscribing line of the molded case is detected (step 320 of FIG. 13). With regard to the detection of the lead coordinates, the coordinates of the four corner portions where leads are disposed is initially determined using the coordinate references shown in FIG. 9, that is, an origin at (0,0) at the upper left and coordinates (1024,511) at the lower right. To explain this by using an image that is presented on the display 94 from the image processing main memory 43, as shown in FIG. 9, block detection and segmentation of the connecting pins are carried out, and the position of each of the four corners is detected from the center coordinates of the blocks 61, 62, 63, and 64 (this is, coordinate pairs $X_1,Y_1$; $X_2,Y_2$; $X_3,Y_3$; and $X_4,Y_4$) at the four corners of the detected blocks. Next, the circumscribing line of the molded case portion of the integrated circuit is prepared based on the position of the four corners. The circumscribing line is prepared as shown by symbol 59 in FIG. 7.

When the circumscribing line of the molded case is prepared as described above, the average quantized binary image data that is memorized in the first binary memory 37, namely, the image data which represents scratches or the like of the molded case portion, is read by the image processing memory 43 (step 330 of FIG. 13). Then the outside of the circumscribing line prepared, as described above, is cleared, this is, removed, with respect to the binary image data that is read, leaving only the image that corresponds to the molded case (step 340 of FIG. 13). This clearing operation is carried out by preparing a rectangle which is somewhat larger in size than the circumscribing line of the mold line, and by clearing the portion 60 (FIG. 8) between the rectangle and the circumscribing line of the molded case.

In this way, the image processing main memory 43 thus contains image data which corresponds to the molded case portion only of the integrated circuit. This is the image, for example, of the region surrounded by the broken line of FIG. 10, and contained within this image data are data regarding scratches 56' and other defects within the molded case portion of the integrated circuit 3. Accordingly, to detect whether there exist scratches in the image data, an orthogonal projection is prepared of the image data within the rectangular region that is indicated by the broken line of FIG. 10, and it is checked to determine if black, (i.e., relatively dark) blocks exists that correspond to scratches within the projected data (steps 350 and 360 of FIG. 13). The vertical projection of the image data is shown by the symbol 67 in FIG. 10. As shown in the projection, there appear black or relatively dark blocks 69 and 70 that correspond to the vertical projection of the scratches 56' within the image data of the rectangular region. When black blocks are detected, the result of the block detection is prepared and memorized as a data table, as shown in FIG. 11. In the data table a detection flag, start address information, X,Y length of the block, and other information is stored.

If black blocks, as described above, namely, defective blocks, are not detected, the integrated circuit 3 is judged to be a conforming article and is directed to and housed in the nondefective article unloader unit 9a (FIG. 1). In judging the black blocks, a rubbing off of 1 bit is judged appropriately as the same block or as noise depending upon the value of the blocks counted so far. Further, the completion of the block detection is judged if two white lines appear consecutively.

Figure 10:
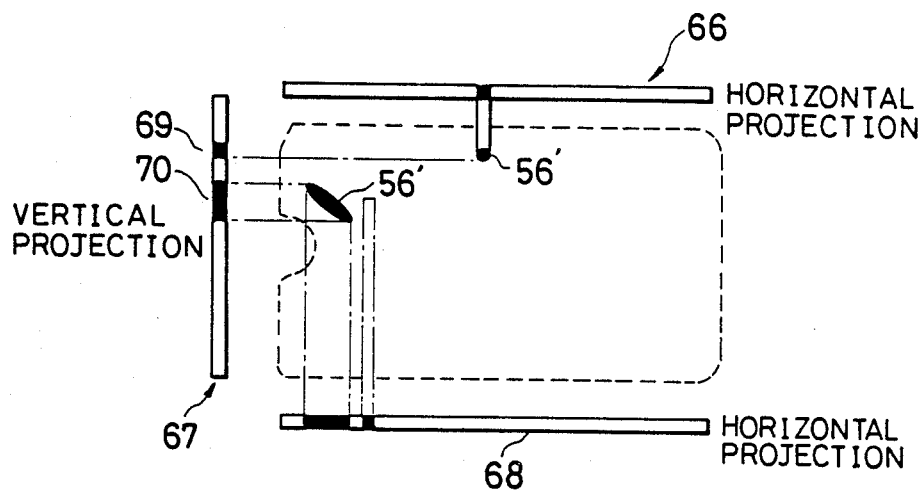
FIG. 10 is a diagram which shows the block detection by horizontal and vertical projection of the integrated circuit image information formed by the apparatus of FIG. 1.

When black blocks are detected as a result of the check of the perpendicularly projected data, horizontal projections, within the range, of the black blocks are prepared, as shown by symbols 66 and 68, of FIG. 10 to carry out a defective block check for the horizontal projections of the black blocks (step 370 of FIG. 13). Here, a noise check, connection of rubbing-offs, and other similar checks are carried out. In doing that, when the sum H+W, where H is the length of the black block detected from the vertical projection and W is the width of the same black block detected from the horizontal projection, is less then a predetermined rated value, it is judged as noise and ignored. Several candidate blocks with H+W values greater than the rated value are selected in the decreasing order of the H+W value, and the black block bit number is calculated for these blocks (step 380 of FIG. 13). When the calculated bit numbers are compared with the predetermined rated number, if there are some with bit numbers greater than the rated number, the integrated circuit 3 is directed to and housed in the defective article housing stick unit 9b (FIG. 1) by evaluating the integrated circuit 3 as defective, and, if there are no bit numbers greater than the predetermine number, the integrated circuit 3 is directed to and housed in the nondefective unloader unit 9a by evaluating the integrated circuit as a conforming article (step 390 of FIG. 13).

The above description has been given in conjunction with the visual appearance inspection of DIP-type integrated circuits of the 300 mil type as an example. However, the present invention is not limited to these types of integrated circuits and can similarly be applied to integrated circuits of flat package configuration, the SIP-type, or the 600 mil type having a larger width. Moreover, lead detection has been done by block detection. However, position detection of the leads is also possible by the pursuit for each line, and preparation of the circumscribing line of the molded case can also be accomplished by that method.

Furthermore, in calculating an average value within the molded case, the average value has been prepared in the horizontal direction. However, accurate quantization of an image of the molded case portion can similarly be accomplished by preparing an average value in the vertical direction.

As described in the foregoing, according to the present invention, a circumscribing line of the case portion of an integrated circuit is prepared from the pin orientation image information which emphasizes the connecting pins of the integrated circuit based on the image information of the observed integrated circuit. In addition, an average image concentration within the circumscribing line of the multi-valued image information obtained by A/D converting the integrated circuit image information pictured into multiple values, and the case image information for the integrated circuit is prepared by quantizing the multi-valued image information within the circumscribing line, based on the average image concentration, and the quality of the case portion of integrated circuit is judged based on the case image information obtained above.

Consequently, the circumscribing line that corresponds to the integrated circuit case portion can be made in a precise manner, and the quantization of the multi-valued image information is carried out by the average concentration of the multi-valued image information within the circumscribing line. Therefore, image information on the case portion alone is extracted, and the inspection of the case portion is carried out accurately and efficiently by the image information, which allows for an increase in the inspection rate of the system shown in FIG. 1 and results in improved inspection reliability and the economization of the inspection process.

It should be mentioned that the above integrated circuit inspection apparatus may be given a configuration in which pin image information which emphasizes the connecting pins of the integrated circuit is prepared by quantizing the integrated circuit image information pictured in a pin image information preparation means in accordance with a predetermined slice level, the size of the pin is calculated in a pin size calculation means based on the pin image information, and the quality of pins is assessed by comparing, in a judging means, the pin size that is calculated in the pin size calculation means with a reference size.

Figure 14A:
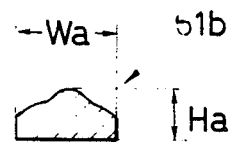
FIGS. 14(a) to 14(c) are diagrams which show representative images of an exemplary connecting pin of an integrated circuit, formed with the apparatus of FIG. 1.
Figure 14B:
Figure 14C:
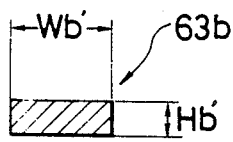

The width W and the height H of the apparent size of each connecting pin of the integrated circuit can be measured by enlarging the pin image information as, for example, shown in FIGS. 14(a) to 14(c). A comparison of the measured sizes with the reference sizes makes it possible to inspect the apparent size of each pin, in particular, the inward or outward bending of connecting pins of the integrated circuit 3 and others.

The image information stored in the second binary memory is displayed emphasizing the connecting pins as shown, for example, in FIG. 5. When the pin image information is enlarged, the enlarged apparent size of each pin is displayed as shown in FIGS. 14(a) to 14(c). From the display, the width W and the height H of each pin are determined, and an inspection of the apparent size of each pin can be carried out by comparing the measured values with the reference sizes.

More specifically, the width and the height, Wa and Ha, respectively, of a normally aligned and defect free connecting pin 61b of a representative integrated circuit 3, as shown in FIG. 14(a), are designated as reference sizes. In addition, enlarged image information of the connecting pins obtained from the pin image information determined in the fixed quantization circuit unit 101B, as described above, are represented by the connecting pins 62b and 63b as shown in FIGS. 14(b) and 14(c). The width and the height of the connecting pins 62b and 63b are indicated by Wa, Hb and Wb', Hb'. These relative sizes of the pins 62b and 63b are compared with the reference sizes. In this comparison, Wb−Wa, Hb−Ha or Wb'−Wa, Hb'−Ha are calculated, and, if the result of the calculation is greater than a predetermined value, for example, "3", it is judged that the pin is bent outward, and, if the result of the calculation is smaller than the predetermined value, the pin is judged to be bent inwardly.

As described above, according to the present invention, pin sizes are calculated from pin image information that emphasizes the connecting pins of integrated circuit by quantizing the integrated circuit image information pictured according to a predetermined slice level, and evaluating the quality of pin by comparing the pin sizes with the reference sizes. Since the sizes of the connecting pin of the integrated circuit can be determined accurately, precise and efficient inspection can be carried out, and, as a result, fast and economical inspection and improved reliability can be realized.

A second embodiment of an inspection apparatus in accordance with the present invention is presented in FIGS. 15 through FIG. 33. The embodiment is constructed so as to prepare positional information regarding the connecting pins of an integrated circuit in a positional information preparation means from image information obtained from the observed integrated circuit. A circumscribing line is prepared from the positional information by a circumscribing line preparation means, and the quality of the integrated circuit case portion is evaluated in a judging means from the image information on the integrated circuit case portion that is surrounded by the circumscribing line.

Figure 15B:
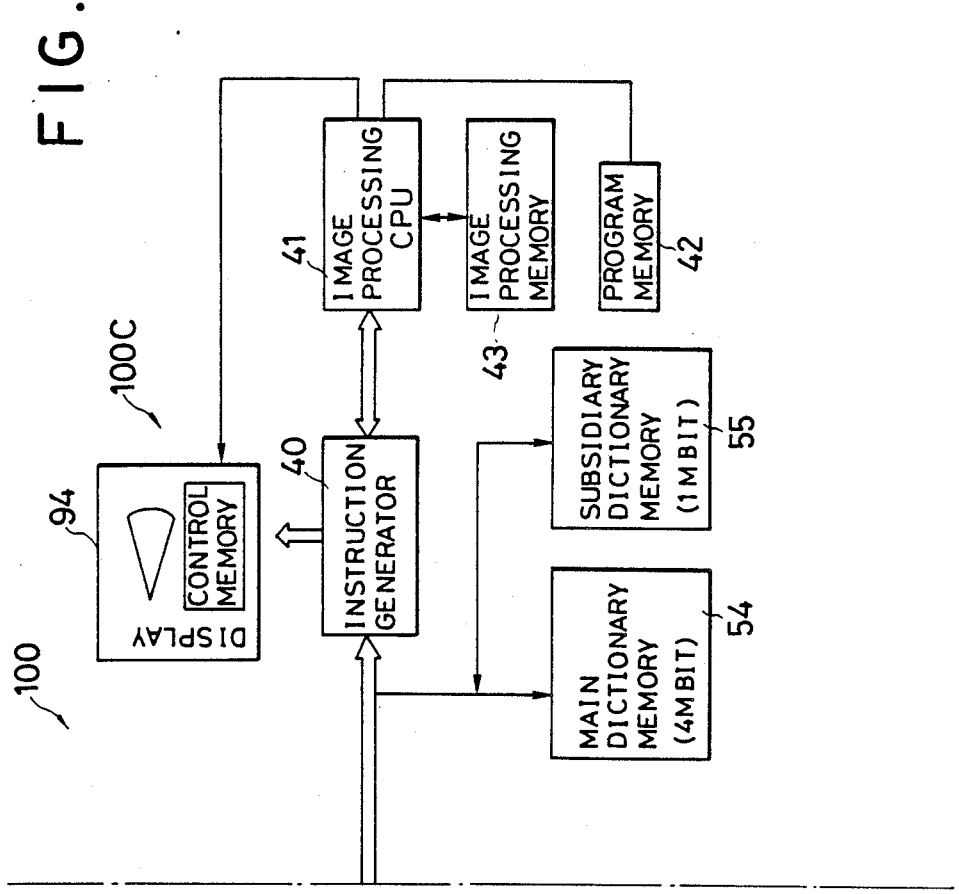

As shown in FIGS. 15A and 15B, the recognition unit 11 includes a first recognition unit 100 connected to the camera 5 which carries out functions (1) to (6), above, and a second recognition unit 101 (FIG. 3) connected to the camera 105 which carries out the function (7), above. The configuration of the first recognition unit 100 is shown in FIGS. 15A and 15B and includes sub-circuits 100A, 100B, 100C and 100D; and the configuration of the second recognition unit 101 is the same as shown in FIG. 3 except that the camera 5 is replaced by the camera 105.

The first recognition unit 100 is arranged on the transporting line 1, and, as shown in FIG. 15, includes the camera 5 which observes the appearance of an integrated circuit 3 as it is transported on the transporting line 1. An image signal of the integrated circuit 3 observed by the camera 5 is amplified by the amplifiers 24 and 25 and is supplied to the A/D converter 26 and the fixed quantization unit 27, respectively. The A/D converter 26 A/D converts the image signal of the integrated circuit 3 to multi-valued data of 8-bit words, that is, one of 256 possible values, and memorizes the multi-valued data in the multi-valued memory 30 via a selector S. The multi-valued memory 30 is connected to the address counter 31 which designates the addressed location in the multi-value memory 30. The multi-valued data pattern of the image signal of the integrated circuit 3 contained in the multi-valued memory 30 is displayed, for example, as shown in FIG. 26. The multi-valued data from the multi-valued memory 30 thus displayed is supplied to the average value preparation unit 33 where the average value of the multi-valued data only in the mold portion of the integrated circuit is calculated. More specifically, the multi-valued data displayed as in FIG. 26, for example, are summed for each line in the horizontal direction, and an average value of the multi-valued data per picture element for each line is calculated by dividing the sum by the number of picture elements in the line.

FIG. 27 shows a diagram for preparing the average value. The multi-valued A/D data that is A/D converted for each line of the image is summed, and the sum is divided by the number x of the picture elements in each line, so that the average value for each line is given by $S_{yn} = \Sigma(A/D)/x$. This average value from the average value preparation unit 33 is stored in the slice memory 34 via a selector S. The address of the slice memory for the average value data corresponds to the number of the vertical line. That is, the average value for each line in the horizontal direction corresponding to each vertical line is memorized in the slice memory 34. The average value memorized in the slice memory 34 is supplied to the A/D pattern quantization unit 36 to carry out quantization of the multi-valued data that is supplied to the A/D pattern quantization unit 36 from the multi-valued memory 30 with the average values as slice data, to form a binary image data. The binary image data from the A/D pattern quantization unit 36 is memorized in the first binary memory 37. In addition, the average value preparation unit 33 is controlled by the average value controller 32, and the slice memory 34 and the first binary memory 37 are supplied with the address information from address counters 35 and 38, respectively. In addition, the A/D pattern quantization unit 36 and the address counters 35 and 38 are controlled by the quantization controller 39.

The circuit blocks from the amplifier 24 to the quantization controller 39 constitutes the multi-valued quantization circuit unit 100A which prepares multi-valued data of the image signal for the integrated circuit 3 and a binary image data from the multi-valued data. The image signal of the integrated circuit 3 from the camera 5 via the amplifier 25 is supplied to the fixed quantization unit 27 where it is converted to a binary image signal by a predetermined slice level, and the binary image signal is memorized in the second binary memory 28 via a selector S.

The quantization by the fixed slice level in the fixed quantization unit 27 is carried out so as to emphasize the connecting pins of the integrated circuit 3, namely, the image of the leads. A lead emphasizing image pattern that is obtained in this way is displayed, for example, as shown in FIG. 5. Address information from the address counter 29 is supplied to the second binary memory 28.

The circuit blocks from the amplifier 25 to the address counter 29 constitutes a fixed quantization circuit unit 100B which prepares a binary image data by carrying out the fixed quantization of the image signal of integrated circuit 3.

The multi-valued quantization circuit unit 100A and the fixed quantization circuit unit 100B are connected to the image bus 200 via various memories, namely, the multi-valued memory 30, the first binary memory 37, the second binary memory 28, and the selectors S. The image bus 200 is connected via the instruction generation unit 40 to the image processing CPU 41 which is connected in turn to the program memory 42 and the image processing main memory 42. The image processing CPU 41, along with the program memory 42 and the image processing main memory 43, controls the overall operation of the first recognition unit 100. In addition, the image processing CPU 41 is connected to the display 94 where the image of the integrated circuit 3 that is observed by the camera 5 is displayed under the control of the image processing CPU 41.

The circuit block from the instruction generation unit 40 to the display 94, with the image processing CPU 41 as the center (FIG. 15), constitutes the central control unit 100C that controls the overall operation of the first recognition unit 100.

In addition, the image bus 200 is connected to a 4M bit main dictionary memory 54 and a 1M bit auxiliary dictionary memory 55. The memories 54 and 55 serve as dictionaries to register and memorize reference data regarding various kinds of standard data regarding the appearance of the integrated circuit structure, printed marks, and size, shape, and orientation of the connecting pins for each of the various integrated circuit types. In more detail, the reference angle $\Theta a$ for marks, the reference orientation angle $\Theta b$ for pins for functions (1) and (2), mentioned above, and so forth will be registered and memorized as be described below. During the appearance inspection of an integrated circuit 3, the reference data memorized in the main and subsidiary dictionaries 54 and 55 are compared with the inspected data to evaluate the quality of integrated circuit 3.

Further, a mark rotation inspection circuit unit 100D is connected to the image bus 200. The mark rotation inspection circuit unit 100D is a circuit unit for carrying out an inspection of the quality of the printed marks by carrying out pattern matching of the printed marks through rotation of the image of the integrated circuit 3 to be inspected to bring it to a coincidence with the reference image, if an integrated circuit 3 to be inspected is observed while it is transported on the transporting line 1 in a crooked or otherwise misaligned position, when the printed marks are to be compared with the reference printed marks contained in the main and auxiliary dictionaries 54 and 55. Namely, the mark rotation inspection circuit unit 100D compares the mark angle $\Theta d$ of a printed mark on an observed integrated circuit 3 that is obtained by the multi-valued quantization circuit unit 100A, the fixed quantization circuit unit 100B, the central control unit 100C, and others, with the mark reference angle $\Theta a$. If the mark angles $\Theta d$ and $\Theta a$ coincide, no mark image rotation is necessary and the mark rotation inspection circuit unit 100D proceeds directly to the pattern matching of the observed and reference marks.

Conversely, if the mark angles $\Theta d$ and $\Theta a$ do not coincide, the difference between the mark angle $\Theta d$ of the observed integrated circuit 3 and the mark reference angle $\Theta a$ is calculated, and the image of the printed mark on the observed integrated circuit 3 is rotated by this difference angle to bring them into coincidence. In order to rotate the observed printed mark of the integrated circuit 3, the mark rotation inspection circuit unit 100D includes an angle detection unit 53, a rotation calculation unit 50, and a rotational quantization memory 44. A rotated image is obtained by setting under the control of the image processing CPU 41 the angle difference, namely, the angle of rotation in the angle detection unit 53, setting the rotation start coordinates $(Xn, Yn)$, the coordinates $(Xa, Ya)$ of the center of rotation and the coordinates $(Xc, Yc)$ of the same center after rotation, in the rotation calculation unit 50, and then setting the image data of the object area of rotation, namely, the image data of the portion of the mark image which is desired to be rotated, in the rotational quantization memory 44. In addition, the angle detection unit 53 is connected to a sine value calculation circuit 51 for calculating the sine value $(\sin \Theta)$ of the rotation angle $\Theta$ and to a cosine value calculation circuit 52 for calculating the cosine value $(\cos \Theta)$ of the rotation angle $\Theta$. The values of the sine and cosine from these circuits are supplied to the rotation calculation unit 50.

The rotated image data is rendered multi-valued in the rotation calculation unit 50 and is memorized in the rotational multi-valued memory 48. The new coordinates of the image after the rotation are given by the following equations.

New X coordinate:

$(Xn-Xa)\times\cos \Theta +(Yn-Ya)\times\sin \Theta +Xc.$

New Y coordinate:

$(Yn-Ya)\times\cos \Theta -(Xn-Xa)\times\sin \Theta +Yc.$

The rotated image data so-obtained is multi-valued data so that it is quantized in a rotational quantization circuit unit 47 based on the slice data which is supplied from a slice data setting unit 46, and the converted binary image data is memorized anew in a rotational quantization memory 44.

Further, the rotational quantization memory 44 and the rotational multi-valued memory 48 are connected to a quantization memory address counter 45 and a multi-valued memory address counter 49, respectively, via respective selectors S. The rotational quantization circuit unit 47 functions to correct the position of the image pattern after the rotation, in addition to the function of quantization. This function can be executed easily by presetting the address for the quantization start in the multi-valued memory address counter 49, and presetting the start address in the quantization memory address counter 45. More specifically, position correction can be accomplished more easily by setting the start address of the rotational quantization memory 44 to the address that corresponds to the position desired to be corrected, in contrast to the start address of the rotational multi-valued memory 48.

The inspection of the printed mark or marks on an integrated circuit 3 to be inspected can be accomplished by carrying out pattern matching between the reference mark and the mark image of the observed integrated circuit 3 obtained by the image rotation as described above.

The first recognition unit 100 comprises the multi-valued quantization circuit unit 100A, the fixed quantization circuit unit 100B, the central control unit 100C, the mark rotation inspection circuit unit 100D, the dictionary memories 54 and 55, and others. Next, its operation, namely, the functions (1) through (6), described above, will be described in the context of FIG. 1, FIG. 2, and FIG. 15 through FIG. 33. First, the measurement of the reference angle $\Theta a$ of the printed mark on a defect free integrated circuit, and its registration in the dictionary, will be described.

The measurement of the mark reference angle $\Theta a$ is carried out by transporting a nondefective integrated circuit 3 on the transporting line 1, and observing the nondefective integrated circuit 3 with the camera 5. The image signal of the nondefective integrated circuit 3 observed with the camera 5 is amplified by the amplifier 24, converted to a multi-valued data of 256 gradations by the A/D converter 26, and is memorized in the multi-valued memory 30. In addition, the average value for each line in the horizontal direction is calculated in the average value preparation unit 33 and is memorized in the slice memory 34. The multi-valued image signal stored in the multi-valued memory 30 is quantized under the control of the A/D pattern quantization unit 36, using the average value in the slice memory 34 as the slice data, and is stored in the first binary memory 37 as a binary image data.

Figure 16:
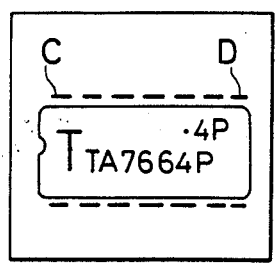
FIG. 16 is a binary image diagram of an integrated circuit formed with the apparatus of FIG. 1.
Figure 17:
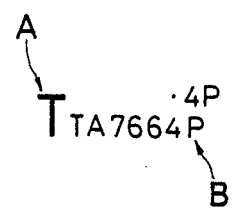
FIG. 17 is a diagram which shows the angle detection point of an integrated circuit mark formed with the apparatus of FIG. 1.

Image information for the integrated circuit 3 observed by the camera 5 and memorized in the first binary memory 37 is represented on the display 94 as a binary image pattern, for example, as shown in FIG. 16, under the control of the image processing CPU 41. Next, the method of determining the reference angle $\Theta a$ of the printed mark on the observed integrated circuit from a binary image data for a nondefective integrated circuit 3 obtained in this manner, will be described.

First, the mark reference angle $\Theta a$ is the angle of alignment of the printed mark. More precisely, it is the angle of the line that connects the upper left corner and the lower right corner of the printed mark. For example and with reference to FIG. 17, the printed marks include a somewhat enlarged T-shaped mark and the alphanumeric strings "TA7664P" and "0.4P" printed on the integrated circuit case. The mark reference angle $\Theta a$ is the angle of the line which connects the upper left corner and the lower right corner, represented respectively by symbols A and B of the mark, with respect to a reference line. In more detail and as shown in FIG. 18, the mark reference angle $\Theta a$ is the angle $\Theta$ between the line AB and the reference line indicated by the generally horizontally aligned broken line in FIG. 18.

Figure 18:
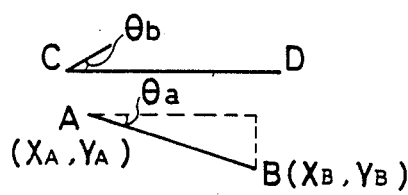
FIG. 18 is a diagram which shows a reference angle detected from a nondefective, that is, defect free, integrated circuit formed with the apparatus of FIG. 1.

When the coordinates (Xa, Ya) and (Xb, Yb) of the points A and B, as shown in FIG. 18, are supplied to the angle detection unit 53 as the coordinate data, the angle is $\Theta a$ determined by calculating the coordinate differences $Xb-Xa$ and $Yb-Ya$ and then $(Yb-Ya)/(Xb-Xa) \times \tan^{-1}$. The value obtained for each kind of integrated circuit is registered and memorized in the dictionary memories 54 and 55 as the respective mark reference angle $\Theta a$ for a defect free integrated circuit 3.

Further, in order to register the printed mark of a binary image data pattern of a nondefective integrated circuit in the dictionary as a reference mark pattern, which is memorized in the first binary memory 37, as described above, and is also displayed on the display 94, the system operator designates, with a cursor, an image pattern presented, for example and as shown in FIG. 28, on the display 94. The printed mark pattern of a nondefective integrated circuit is segmented by receiving the coordinate data of the cursor frame, and a standard mark pattern, a somewhat thicker mark pattern, a somewhat thinner mark pattern, and so on are prepared, as shown in FIGS. 23 to 25. The various mark patterns are stored in the dictionary memories 54 and 55 for each of the various kinds of integrated circuits according to a preferred memory configuration, for example, as shown in FIG. 32. As shown therein, the mark pattern storage memory configuration includes information as to the kind or type of integrated circuit, a start address, the X and Y sizes, the standard pattern, the thicker pattern, and the thinner pattern with this sequence recurring for the various types of integrated circuits for which reference information is desired.

Next, the measurement and registration in the dictionary of the reference orientation angle $\Theta b$ of the connecting pins of a nondefective integrated circuit, namely, the inclination angle $\Theta b$ of the orientation of the connecting pins of the integrated circuit, will be described.

The measurement of the reference orientation angle $\Theta b$ of the connecting pins of a defect free integrated circuit is carried out in a manner analogous to the measurement of the mark reference angle $\Theta a$, that is, by transporting a nondefective integrated circuit 3 on the transporting line 1 and by forming an image of the observed nondefective integrated circuit 3 with the camera 5. The image signal of the nondefective integrated circuit 3 provided by the camera 5 is amplified by the amplifier 25 (FIG. 15A) and is converted in the fixed quantization unit 27 to a binary image data which emphasizes the connecting pins of the integrated circuit, as shown, for example, in FIG. 5, and with the binary image data stored in the second binary memory 28. For instance, if both ends of the connecting pins are called C and D (FIGS. 16–21), the coordinates of the points C and D can be determined, as described above for the printed marks, so that the inclination angle $\Theta b$ (FIG. 18) of the line CD that connects these points, namely, the reference orientation angle $\Theta b$ of the connecting pins, can be determined from the coordinate data in a manner analogous to that described above. The value of the reference orientation angle $\Theta b$ is stored and memorized in the dictionary memories 54 and 55 as the pin reference orientation angle $\Theta b$ for the various types of integrated circuits for which reference information is desired.

Further, an angle $\Theta_1$, between the line CD and line AB equals the sum of the angle $\Theta a$ and the angle $\Theta b$, and these reference angles $\Theta a$, $\Theta b$, and $\Theta_1$ are registered in the dictionary memories 54 and 55 in the form of a table for the various types of integrated circuits, as shown in FIG. 33. As shown therein, the memories 54 and 55 are configured to store information as to the kinds of integrated circuit, the angles $\Theta a$ and $\Theta b$, and their sum $\Theta_1$.

When the reference data, namely, the mark reference angle $\Theta a$, the pin reference orientation angle $\Theta b$, the angle $\Theta_1$, the standard printed mark pattern, and so forth are prepared and registered in the dictionary memories 54 and 55, as described above, the actual inspection for each integrated circuit is based on the stored reference data. In addition, for those various types of integrated circuits 'registered' in the dictionary memories 54 and 55, as described above, there is no need for preparing a dictionary again, and inspection can be carried out immediately.

First, an inspection of the skew orientation of the printed mark of an integrated circuit to be inspected, that is, an inspection to determine if the printed mark is printed in a crooked or misaligned manner, from the measurement of the observed pin orientation angle $\Theta c$ and the observed printed mark angle $\Theta d$ of an integrated circuit to be inspected, and the reference angles $\Theta a$ and $\Theta b$, will be described.

The integrated circuit 3 to be inspected is transported on the transporting line 1 and is observed by the camera 5. The image signal from the camera 5 is converted to multi-valued data in the multi-valued quantization circuit unit 100A via the amplifier 24 and memorized in the multi-valued memory 30. Concurrently, the image signal from the camera 5 is also quantized and memorized in the first binary memory 37 as a binary image data. The image signal is fixed-quantized by the fixed quantization circuit unit 100B via the amplifier 25, and is memorized in the second binary memory 28 as a binary image data that emphasizes the connecting pins.

In many cases, an integrated circuit 3 to be inspected is not transported on the transporting line 1, with its long axis consistently aligned in the direction of transportation. Oftentimes, the integrated circuits 3 are transported in a crooked, skewed, or otherwise misaligned manner along the transporting line. Moreover, in contrast to the method by which the reference data is prepared, it is necessary to segment automatically the mark area of integrated circuit and, thus, it becomes necessary to determine position information for the integrated circuit. The position information of an integrated circuit is determined from the integrated circuit leads, namely, the positions and the orientation angle of the connecting pins, from the binary image information that emphasizes the position of the connecting pins. This information is stored in the second binary memory 28 (FIG. 15) and allows determination of the inclination angle of the integrated circuit and the position of the mark containing area on the integrated circuit case.

Figure 19:
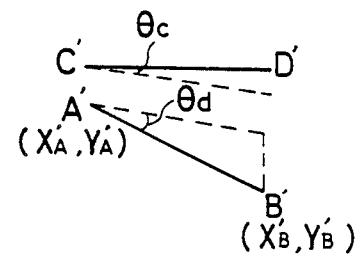
FIG. 19 is a diagram which shows angles detected from an integrated circuit formed with the apparatus of FIG. 1.

The position detection of the connecting pins of integrated circuit is carried out, in a manner analogous to the case of preparing the dictionary, by detecting those block that represent the connecting pins from the binary image information stored in the second binary memory 28, which information emphasizes the connecting pins, prepare position information for the connecting pins from the block information, and determination of the orientation angle $\Theta c$ of the connecting pins from the position information. When both end points of the connecting pins are called C' and D', as shown in FIG. 19, the angle of the line C'D' with respect to the reference line shown by the broken line is the pin orientation angle $\Theta c$ of the observed integrated circuit 3.

Figure 21:
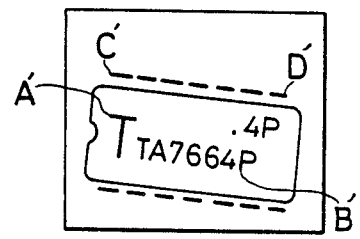
FIG. 21 and FIG. 22 are diagrams which show examples of detection mark pattern of an integrated circuit, taken with the apparatus of FIG. 1.
Figure 22:
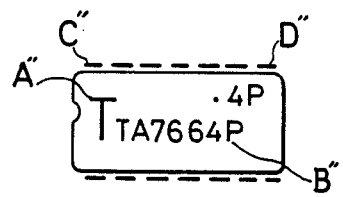

In order to detect the mark area of the observed integrated circuit, the binary image data of the integrated circuit stored in the first binary memory 37, namely, the mold image data in this case, is read into the image processing main memory 43 to prepare vertical and horizontal projections for the mold image data. The vertical projection and the horizontal projection represent the overall presence or absence of the mold image data as seen from the vertical and the horizontal directions. For instance, if there is a mark in a portion of the mold area, information corresponding to the mark at the portions corresponding to the mark appears in the vertical projection and the horizontal projection of the mold area. Accordingly, if there is a printed mark within the mold area, then by preparing the vertical and the horizontal projections of the mold area it is possible to know the position of the mark, that is, the mark area. Hence, when the upper left corner point and the lower right corner point of the mark area determined in this way by the vertical and horizontal projections are called A' and B', the angle of the line A'B' with respect to a reference line is the printed mark angle $\Theta d$ as mentioned earlier. FIG. 19 illustrates the line A'B' that connects the points A' and B' and the printed mark angle $\Theta d$ of an observed integrated circuit 3 to be inspected. In addition, FIG. 21 and FIG. 22 show examples of detection mark patterns.

Figure 20:
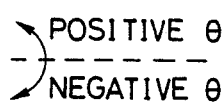
FIG. 20 is a diagram which shows the positive and negative directions for the angles in FIG. 18 and FIG. 19.

By comparing the sum of the angles $\Theta c + \Theta d$ obtained from the pin orientation angle $\Theta c$ and the printed mark angle $\Theta d$ obtained from the observed integrated circuit 3, determined in the manner described above, with the reference angle $\Theta_1 (= \Theta a + \Theta b)$ that is determined as described from a defect free integrated circuit 3 and memorized in the dictionary memories 54 and 55, it is possible to determine if the mark or marks of the observed integrated circuit 3 is printed in a misaligned or crooked manner. In summing the angles and as shown in FIG. 20, the sign for each angle is plus when the angle increases in the counterclockwise direction and is minus when the angle increases in the clockwise direction.

Next, rubbing-offs, chips, or the like in the printed marks of the integrated circuit to be inspected will be described. This is done by checking the orientation angle of the mark of the integrated circuit 3 to be inspected against the reference mark registered, based on the pin orientation angle $\Theta c$ and the printed mark angle $\Theta d$ of the integrated circuit 3 to be inspected as determined above. If the orientation angles coincide, the quality of the printed mark may be assessed by matching the image data patterns of both marks without special problems.

However, if the orientation angle of the mark on the integrated circuit 3 to be inspected and the orientation angle of the reference mark do not coincide, pattern matching is carried out after rotating the mark of the integrated circuit 3 to be inspected to bring it into coincidence with the reference mark. For this purpose, the difference between the orientation angles of both marks, namely, the angle of rotation, coordinates of rotation start point, coordinates of the center of rotation, coordinates of the same center after rotation, image information of the object area of rotation, and others are provided in the mark rotation inspection circuit unit 100D, as mentioned earlier, to store a rotated image data that has a mark orientation which coincides with that of the reference mark, in the rotational multi-valued memory 48 as multiple values. Then, the rotated image data is binary coded in the rotational quantization circuit unit 47 to store it in the rotational quantization memory 44 as a binary image data. Then, pattern matching is performed between a binary image data of the mark that has an orientation angle equal to that of the reference mark after rotation, and the data of the reference mark, inspecting defects in the printed mark. For instance, if a defective portion in the form of a chip is detected in the somewhat enlarged T-shaped symbol, as shown in FIG. 31, as a result of pattern matching between a printed mark detected, as shown in FIG. 29, and a somewhat thin reference pattern, as shown in FIG. 30, the mark is judged defective.

As in the above, in the first recognition unit 100, a mark reference angle $\Theta a$ and a pin reference orientation angle $\Theta b$ are prepared from a defect-free integrated circuit, and these values are registered as a dictionary reference values to be utilized for the inspection. In addition, the pin orientation angle $\Theta c$ and the printed mark angle $\Theta d$ of an observed integrated circuit to be inspected are detected, and the skew of the printed mark is detected by a comparison of the sum of the angles $\Theta c$ and $\Theta d$ with the sum of the registered reference angles $\Theta a$ and $\Theta b$. Moreover, the difference of the orientation angle of the detected printed mark with respect to that of the reference printed mark is calculated, and the quality of the printed mark is judged by carrying out a pattern matching between both images after providing a correction to the image data of the mark by rotating it by an angle equal to the calculated difference.

The second recognition unit 101 performs an inspection for defects, such as scratches, in the integrated circuit molded case, that is, function (7), above, and comprises a camera 105, in place of camera 5, for observing the appearance image of the integrated circuit, the multi-valued quantization circuit unit 101A, the fixed quantization circuit unit 101B, and the central control unit 101C, as shown in FIG. 3. These circuit units are connected to each other via the image bus 300.

The multi-valued quantization circuit unit 101A is a circuit unit which prepares and memorizes a multi-valued image data using an image signal from the camera 105, and prepares and memorizes a binary image data from the multi-valued image data, and has the same configuration and function as the multi-valued quantization circuit unit 100A of the first recognition unit 100, with the same components designated by the same reference characters.

The fixed quantization circuit unit 101B is a circuit unit which prepares and memorizes a binary image data by quantizing the image signal from the camera 105 at a fixed slice level, and has the same configuration and function as the fixed quantization circuit unit 100B of the first recognition unit 100, and the same components are given by identical symbols.

Further, the central control unit 101C is a circuit unit which controls the overall operation of the second recognition unit 101, and has an instruction generation unit 40, an image processing CPU 41, a program memory 42, and an image processing main memory 43, with similar configuration as the central control unit 100C of the first recognition unit 100, and, in addition, has a support CPU 61 and an interface 63 for the CPU.

The operation of the second recognition unit 101 with the above configuration, namely, the operation of inspecting for defects such as scratches, chips, and cracks in the molded case of the integrated circuit to be inspected, is similar to that described in conjunction with FIG. 1 and FIG. 3 to FIG. 13, so that further description will be omitted.

As described in the foregoing, according to the present invention, the quality of the case portion of an object to be inspected is carried out by preparing position information of the connecting pins of the object to be inspected from image information of the observed object that is obtained by from the observing camera, and by judging the image information of the case portion of the object to be inspected surrounded by a circumscribing line of the case portion of the object to be inspected that is prepared from the position information. Since, therefore, it is possible to extract accurately only the image information of the case portion of the object to be inspected, and carry out a precise and efficient inspection of the required case portion alone, quick and economical inspection and an improved reliability of the inspection can be achieved.

In addition, according to the present invention, from mark image information in the image information obtained by taking a picture of a nondefective article that serves as a reference, a reference angle with respect to a predetermined reference line is detected and the angle is registered as a reference angle. Further, the quality of the mark position of the object to be inspected is judged, by detecting an inclination angle with respect to the reference line of the mark of the object to be inspected from the mark image information in the image information obtained by taking a picture of the object to be inspected, and by comparing the detected inclination angle with the reference angle. Moreover, the quality of the mark of the object to be inspected is judged by detecting the mark image information of the object to be inspected from the image information of the object to be inspected obtained from the picture of the object to be inspected, detecting the inclination angle of the mark of the object to be inspected with respect to the predetermined reference line is detected from the mark image information, detecting the difference between the inclination angle and the reference angle, forming a rotated image information by rotating the mark image information by the difference in angle, and by comparing the rotated mark image information of the object to be inspected with the reference mark image information. Accordingly, it is possible to inspect accurately the bending of the mark by the use of the angle information that is registered as the reference information. In addition, the mark position of the object to be inspected can be corrected by rotating the mark image based on the angle information, and scratches, rubbing-offs, chips, and so on in the mark can be inspected accurately and quickly by taking a pattern matching between the mark image information that is corrected by rotation and the reference mark image information. Therefore, it is possible to realize improvement in reliability and economy of the inspection.

Moreover, according to the present invention, the image information that is obtained by taking a picture of the object to be inspected is quantized and memorized in the quantization memory means, the quantized image information is rendered multiple valued after rotating it and is memorized in the multi-valued memory means. Accordingly, the rotation of the image information is carried out through bit processing, without requiring particularly a serial-parallel transformation processing or specifying a rotational image memory means. Therefore, the inspection by means of the pattern matching of the image information can be accomplished effectively and precisely.

In the present embodiment, the quantization circuit of the image information pictured by the camera and the quantization circuit for rotating the image information are constructed separately. However, it is not limited to this case, and it is possible to realize both functions by constructing them using an identical system. In this case, it is not necessary to transfer the information for rotation of the image, and it is possible to start the rotation immediately.

Still further, in the above embodiments, description has been given in connection with the appearance inspection of integrated circuit as an example. However, the present inspection is not limited to that case alone, and can be applied also to other members.

Thus it will be appreciated from the above that as a result of the present invention, a highly effective inspection apparatus is provided by which the principal objective, among others, is completely fulfilled. It will be equally apparent and is contemplated that modification and/or changes may be made in the illustrated embodiment without departure from the invention. Accordingly, it is expressly intended that the foregoing description and accompanying drawings are illustrative of preferred embodiments only, not limiting, and that the true spirit and scope of the present invention will be determined by reference to the appended claims and their legal equivalent.

What is claimed is:

1. An apparatus for inspecting the molded case portion of an IC device having connecting pins for connecting the IC device to other members, comprising:
    imaging means for taking an image of the IC device to be inspected;
    means for deriving positional information of the connecting pins from the image;
    means for making a circumscribing line enclosing the molded case portion of the image of the IC device in accordance with the positional information of the connecting pins; and
    means for judging quality of the molded case portion from the image inside the circumscribing line.

2. The apparatus as claimed in claim 1 wherein the deriving means derives the positional information of the connecting pins as a function of the pin orientation image in which the connecting pins are emphasized by quantizing the image according to a predetermined slice level.

3. The apparatus as claimed in claim 1 wherein the judging means includes means for obtaining projection information regarding projections of the image of the molded case portion.

4. The apparatus as claimed in claim 1 further comprising means for deducing multi-valued image information defined by the circumscribing line.

5. The apparatus as claimed in claim 4 further comprising means for determining an average image density within the circumscribing line of the multi-valued image information.

6. The apparatus as claimed in claim 5 further comprising means for quantizing the multi-valued image information within the circumscribing line on a basis of the averaged image density in order to obtain case image information indicating image of the molded case portion enclosed inside the circumscribing line.

7. The apparatus as claimed in claim 6 wherein the judging means judges the quality of the molded case portion as a function of the case image information.

8. The apparatus as claimed in claim 7 wherein the judging means includes means for obtaining projection information to be utilized in judging the quality of structure of the molded case portion.

9. The apparatus as claimed in claim 1 wherein the making means includes means for deriving pin image information in which the connecting pins are emphasized by quantizing the image taken by the imaging means according to a predetermined slice level.

10. The apparatus as claimed in claim 9 wherein the making means includes means for calculating the size of the connecting pins from the pin image information.

11. The apparatus as claimed in claim 10 wherein the judging means also judges quality of the connecting pins by comparing the calculated size of the connecting pins with a reference size.

* * * * *